(12) United States Patent
MacConnell

(10) Patent No.: US 9,933,408 B2
(45) Date of Patent: Apr. 3, 2018

(54) METHOD FOR CHARACTERIZING THE HYDROCARBON CONTENT OF A REFORMATE STREAM

(71) Applicant: AIR PRODUCTS AND CHEMICALS, INC., Allentown, PA (US)

(72) Inventor: Matthew H. MacConnell, Orefield, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 764 days.

(21) Appl. No.: 14/536,949

(22) Filed: Nov. 10, 2014

(65) Prior Publication Data

US 2016/0131631 A1 May 12, 2016

(51) Int. Cl.
| | | |
|---|---|---|
| G01N 9/00 | (2006.01) | |
| G01N 33/28 | (2006.01) | |
| G01N 30/88 | (2006.01) | |
| G01N 9/32 | (2006.01) | |
| B01D 53/58 | (2006.01) | |

(52) U.S. Cl.
CPC ......... *G01N 33/2835* (2013.01); *B01D 53/58* (2013.01); *B01D 2256/24* (2013.01); *B01D 2257/40* (2013.01); *B01D 2257/406* (2013.01); *C01B 2203/0233* (2013.01); *G01N 9/32* (2013.01); *G01N 2030/8854* (2013.01); *Y10T 436/21* (2015.01)

(58) Field of Classification Search
CPC .................................................. G01N 33/2835
USPC ........................................................ 436/143
See application file for complete search history.

(56) References Cited

U.S. PATENT DOCUMENTS

| 2,768,986 | A | * | 10/1956 | Lien ........................ C07C 7/152 |
|---|---|---|---|---|
| | | | | 208/324 |
| 6,143,202 | A | | 11/2000 | Christensen et al. |
| 6,376,114 | B1 | * | 4/2002 | Bonville, Jr. ..... H01M 8/04089 |
| | | | | 429/425 |
| 6,758,101 | B2 | | 7/2004 | Valentine |
| 7,037,485 | B1 | | 5/2006 | Dmevich et al. |
| 7,871,826 | B2 | | 1/2011 | Peng et al. |
| 8,137,422 | B2 | | 3/2012 | Licht et al. |
| 8,425,763 | B2 | * | 4/2013 | Tatarchuk .............. B01D 53/02 |
| | | | | 208/246 |

(Continued)

FOREIGN PATENT DOCUMENTS

| CA | 02842984 | 3/2013 |
|---|---|---|
| JP | 10120401 | 5/1998 |

(Continued)

OTHER PUBLICATIONS

GASSTM-2040, Gas Analysis Sampling System, User Manual, v1.20, Perma Pure, downloaded from www.permapure.com on Oct. 20, 2014.

*Primary Examiner* — Christine T Mui
*Assistant Examiner* — Emily R. Berkeley
(74) *Attorney, Agent, or Firm* — Bryan C. Hoke, Jr.

(57) ABSTRACT

Method for characterizing the hydrocarbon content of a reformate sample stream comprising methane, water, carbon monoxide, ammonia, and hydrogen from a steam-hydrocarbon reforming process. Water and ammonia are removed from the reformate sample stream and the hydrocarbon content of the reformate sample stream depleted in water and ammonia is measured using a chemical component analyzer.

14 Claims, 1 Drawing Sheet

(56) References Cited

U.S. PATENT DOCUMENTS

| | | |
|---|---|---|
| 8,440,107 B2 | 5/2013 | Tadd et al. |
| 8,580,153 B2 | 11/2013 | Vauk et al. |
| 8,591,769 B2 | 11/2013 | Vauk et al. |
| 8,591,861 B2 | 11/2013 | Lomax et al. |
| 2001/0032965 A1 | 10/2001 | Wang |
| 2002/0178806 A1 | 5/2002 | Valentine |
| 2002/0096208 A1 | 7/2002 | Jensen et al. |
| 2002/0019719 A1 | 12/2002 | Epp et al. |
| 2005/0126642 A1* | 6/2005 | Lillis ................. C25B 15/08 137/606 |
| 2009/0094894 A1 | 4/2009 | Genkin et al. |
| 2009/0232729 A1 | 9/2009 | Genkin et al. |
| 2010/0224834 A1 | 9/2010 | Peng et al. |
| 2014/0134547 A1 | 5/2014 | Tonkovich |

FOREIGN PATENT DOCUMENTS

| | | |
|---|---|---|
| WO | 2009090351 A1 | 7/2009 |
| WO | 2013/002752 | 1/2013 |

\* cited by examiner

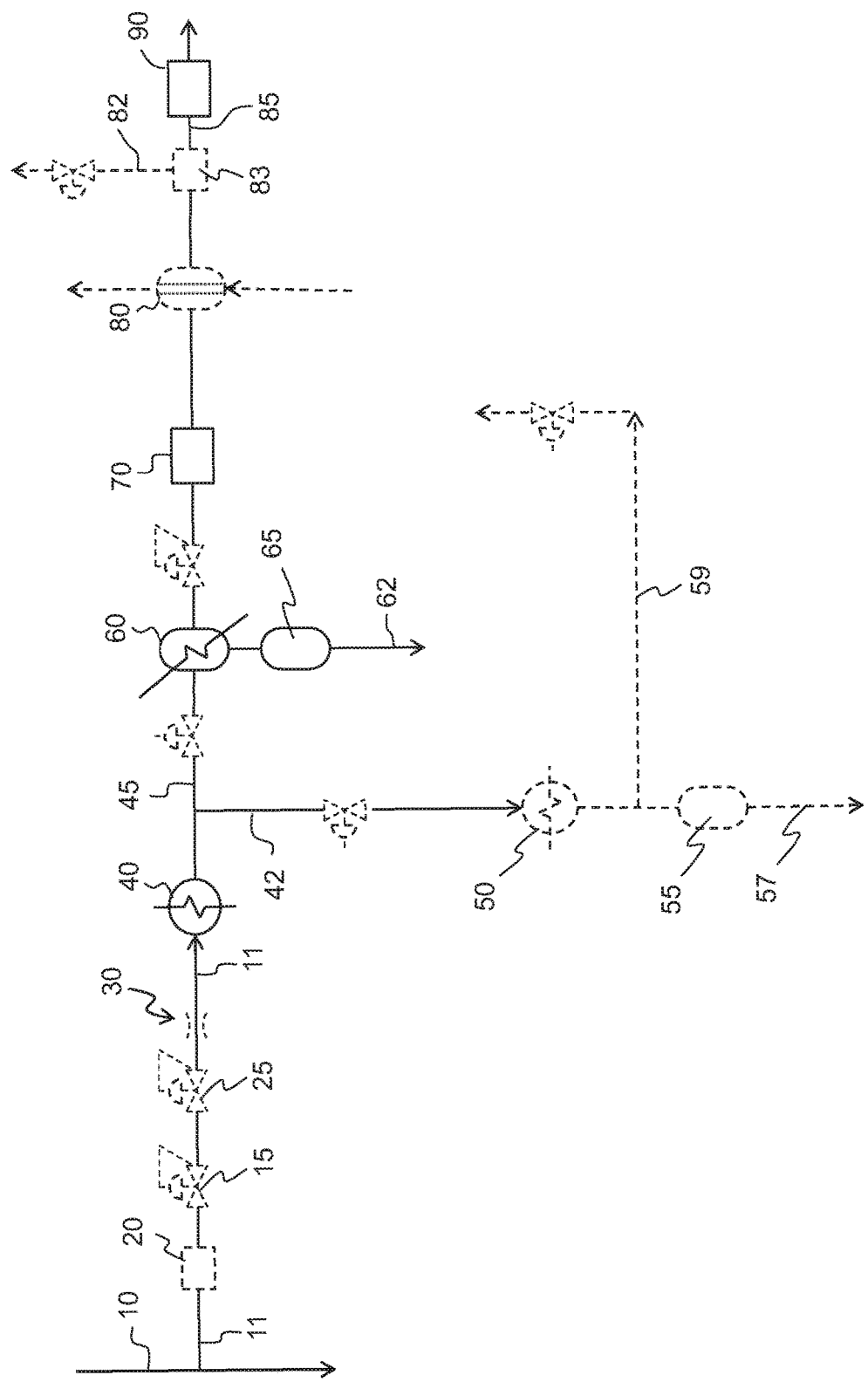

METHOD FOR CHARACTERIZING THE HYDROCARBON CONTENT OF A REFORMATE STREAM

CO-FILED APPLICATION

This application is contemporaneously filed with U.S. patent application Ser. No. 14/537,095, now U.S. Pat. No. 9,409,095, titled "Steam-Hydrocarbon Reforming Process", incorporated herein by reference.

BACKGROUND

The present invention relates to steam-hydrocarbon reforming processes in general, and more specifically to a method for characterizing the hydrocarbon content in a reformate sample stream.

Industry desires to improve reformer energy efficiency and productivity.

To improve energy efficiency and productivity, measurements of hydrocarbon content in various intermediate streams can be made and control of the reforming process improved through use of the measurements.

For example, it is found to be useful to measure the hydrocarbon content of intermediate process streams of a steam-hydrocarbon reforming process so that the steam flow rate in the feed to the process is adjusted to provide the desired conversion of hydrocarbon feedstock with improved energy efficiency.

The challenge to measuring the hydrocarbon content of intermediate process stream of a steam-hydrocarbon reforming process is due to the high pressure and high temperature of the intermediate stream along with the high water content and ammonia content. Commercial sampling systems designed for measuring the flue gas of combustion systems are not suited for measuring intermediate streams from a steam-hydrocarbon reforming process.

BRIEF SUMMARY

The present invention relates to a method for characterizing a hydrocarbon content of a reformate sample stream.

There are several aspects of the invention as outlined below. In the following, specific aspects of the invention are outlined below. The reference numbers and expressions set in parentheses are referring to an example embodiment explained further below with reference to the FIGURES. The reference numbers and expressions are, however, only illustrative and do not limit the aspect to any specific component or feature of the example embodiment. The aspects can be formulated as claims in which the reference numbers and expressions set in parentheses are omitted or replaced by others as appropriate.

Aspect 1. A method for characterizing a hydrocarbon content of a reformate sample stream (11), the method comprising:
(a) withdrawing the reformate sample stream (11) from a steam-hydrocarbon reforming process, the reformate sample stream (11) comprising $CH_4$, $H_2O$, CO, $NH_3$, and $H_2$;
(b) cooling the reformate sample stream (11) in a first heat exchanger (40) to condense a portion of the $H_2O$ in the reformate sample stream (11) thereby forming a liquid fraction and a vapor fraction;
(c) dividing the reformate sample stream from step (b) into a vapor fraction-enriched stream (45) having a time-averaged mass flow rate, $F_1$, and a liquid fraction-enriched stream (42) having a time-averaged mass flow rate, $F_2$,
(d) cooling the vapor fraction-enriched stream (45) to within a temperature ranging from 0° C. to 10° C. or ranging from 2° C. to 7° C. to condense $H_2O$ in the vapor fraction-enriched stream;
(e) removing at least a portion of the condensed $H_2O$ (62) from the vapor fraction-enriched stream (45) from step (d);
(f) passing the vapor fraction-enriched stream (45) from step (e) to an ammonia removal unit (70) to remove $NH_3$ from the vapor fraction-enriched stream (45); and
(g) passing at least a first portion (85) of the vapor fraction-enriched stream (45) from step (f) to a chemical component analyzer (90) to measure the hydrocarbon content in the at least a first portion (85) of the vapor fraction-enriched stream (45).

Aspect 2. The method of aspect 1 wherein the vapor fraction-enriched stream from step (f) is passed to a dryer to further remove $H_2O$ in the vapor fraction-enriched stream prior to passing the at least a first portion (85) of the vapor fraction-enriched stream (45) to the chemical component analyzer (90).

Aspect 3. The method of aspect 1 or aspect 2 wherein the reformate sample stream (11) has an $H_2O$ mole fraction greater than 0.35 or greater than 0.5.

Aspect 4. The method of any one of aspects 1 to 3 wherein $F_1$ and $F_2$ are controlled such that $$\frac{F_1}{F_1 + F_2} \le 0.2.$$

Aspect 5. The method of any one of aspects 1 to 4 further comprising passing the reformate sample stream (11) through a conduit from a reformate sample stream source to the first heat exchanger (40) while heating the reformate sample stream (11) in the conduit in an amount sufficient to prevent condensation of the $H_2O$ in the reformate sample stream in the conduit.

Aspect 6. The method of any one of aspects 1 to 5 wherein the at least a portion of the condensed $H_2O$ (62) from the vapor fraction-enriched stream is removed using a liquid drain trap (65).

Aspect 7. The method of any one of aspects 1 to 5 wherein the at least a portion of the condensed $H_2O$ (62) from the vapor fraction-enriched stream is removed using a liquid drain trap (65) and a coalescing filter.

Aspect 8. The method of any one of aspects 1 to 7 wherein the ammonia removal unit comprises phosphoric acid.

Aspect 9. The method of any one of aspects 1 to 8 further comprising: rejecting a second portion (82) of the vapor fraction-enriched stream (45) from step (f) where the second portion is not passed to the chemical component analyzer (90), wherein the at least a first portion (85) of the vapor fraction-enriched stream (45) has a time-averaged mass flow rate $V_1$, the second portion of the vapor fraction-enriched stream has a time-averaged mass flow rate, $V_2$, where $$\frac{V_1}{V_1 + V_2} \le 0.1 \text{ or } 0 < \frac{V_1}{V_1 + V_2} \le 0.1.$$

Aspect 10. The method of any one of aspects 1 to 9 wherein the vapor fraction-enriched stream is cooled in step (d) in a second heat exchanger wherein the second heat exchanger comprises a vortex tube wherein compressed air is introduced into the vortex tube to provide the cooling of the vapor fraction-enriched stream.

Aspect 11. The method of any one of aspects 2 to 10 wherein the dryer is a membrane dryer.

Aspect 12. The method of aspect 11 wherein dry $N_2$ or dry air is introduced into the membrane dryer (80) as a purge gas to assist in the removal of $H_2O$ from the vapor fraction-enriched stream (45).

Aspect 13. The method of any one of aspects 1 to 12 wherein the chemical component analyzer is a gas chromatograph.

Aspect 14. The method of any one of aspects 1 to 13 wherein the hydrocarbon content measured in step (g) is a C2+ hydrocarbon content in the at least a first portion (85) of the vapor fraction-enriched stream (45).

Aspect 15. The method of any one of aspects 1 to 14 further comprising:

passing a feed stream to a reactor, the feed stream containing hydrocarbons including C2+ hydrocarbons;

reacting the feed stream in the reactor under reaction conditions sufficient to react the feed stream and form a reactor product stream (10) comprising $CH_4$, $H_2O$, CO, $NH_3$, and $H_2$;

withdrawing the reactor product stream (10) from the reactor;

dividing the reactor product stream (10) into at least two portions, namely a first reactor product stream and the reformate sample stream (11), thereby withdrawing the reformate sample stream (11) from the steam-hydrocarbon reforming process in step (a); and providing the first reactor product stream to a processing unit of the steam-hydrocarbon reforming process for further processing.

Aspect 16. The method of the preceding aspect wherein the reactor is a prereformer or a catalytic steam-hydrocarbon reformer or a shift reactor.

Aspect 17. The method of aspect 15 or aspect 16 wherein the processing unit is a catalytic steam-hydrocarbon reformer or a shift reactor or a separation unit for producing a hydrogen-enriched product by a separation process.

Aspect 18. The method of any one of aspects 15 to 17 wherein the reactor is a prereformer and the processing unit is a catalytic steam-hydrocarbon reformer, or wherein the reactor is a catalytic steam-hydrocarbon reformer and the processing unit is a shift reactor or a separation unit for producing a hydrogen-enriched product by a separation process or a shift reactor, or wherein the reactor is a shift reactor and the processing unit is a separation unit for producing a hydrogen-enriched product by a separation process.

Aspect 19. The method of any one of aspects 15 to 18 wherein the feed stream contains steam, the feed stream having a molar flow rate of hydrocarbons, $F_{HC}$, and a molar flow rate of steam, $F_S$, thereby defining a ratio, $F_S/F_{HC}$, of the molar flow rate of steam to the molar flow rate of hydrocarbons in the feed stream (21), the process further comprising:

controlling the ratio of the molar flow rate of steam to the molar flow rate of hydrocarbons based on the measured hydrocarbon content in the at least a first portion (85) of the vapor fraction-enriched stream (45).

BRIEF DESCRIPTION OF SEVERAL VIEWS OF THE DRAWINGS

The sole FIGURE is a process flow diagram for the method for characterizing the hydrocarbon content of a reformate sample stream.

DETAILED DESCRIPTION OF THE PREFERRED EMBODIMENTS

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention, it being understood that various changes may be made in the function and arrangement of elements without departing from scope of the invention as defined by the claims.

The articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

The adjective "any" means one, some, or all indiscriminately of whatever quantity.

The phrase "at least a portion" means "a portion or all." The at least a portion of a stream may have the same composition with the same concentration of each of the species as the stream from which it is derived. The at least a portion of a stream may have a different concentration of species than that of the stream from which it is derived. The at least a portion of a stream may include only specific species of the stream from which it is derived.

As used herein, "first," "second," "third," etc. are used to distinguish from among a plurality of steps and/or features, and is not indicative of the total number, or relative position in time and/or space unless expressly stated as such.

The term "depleted" means having a lesser mole % concentration of the indicated gas than the original stream from which it was formed. "Depleted" does not mean that the stream is completely lacking the indicated gas.

The terms "rich" or "enriched" means having a greater mole % concentration of the indicated gas than the original stream from which it was formed.

The present invention relates to a method for characterizing a hydrocarbon content of a reformate sample stream, where the reformate sample stream comprises $CH_4$, $H_2O$, CO, $NH_3$, and $H_2$. The reformate sample stream may have an $H_2O$ mole fraction greater than 0.35 or greater than 0.5.

The method is discussed with reference to the sole FIGURE.

The hydrocarbon content may be expressed in any convenient form, for example as a concentration of the various hydrocarbon species on a dry basis, as a ratio of one hydrocarbon species to the total hydrocarbon species content, or as a ratio of one species to another species.

The reformate sample stream source 10 may be from any location in a reforming process where hydrocarbon feedstock has undergone some reaction by reforming, for example, from a location between a prereformer and a catalytic steam-hydrocarbon reformer, from a location between a catalytic steam-hydrocarbon reformer and a shift reactor, or between a shift reactor and a pressure swing adsorber.

Since the pressure of the reformate sample stream 11 will typically be greater than that desired for measurement, the pressure of the reformate sample stream 11 may be reduced through any number of valves 15, 25, orifices 30, and the like. The reformate sample stream 11 may be filtered in filter 20, if desired.

The method comprises cooling the reformate sample stream 11 in a first heat exchanger 40 to condense a portion of the $H_2O$ in the reformate sample stream 11 thereby forming a liquid fraction and a vapor fraction. The first heat exchanger 40 may be an ambient air-cooled heat exchanger.

The reformate sample stream 11 may be passed through a conduit from the reformate sample stream source to the first heat exchanger 40 while heating the reformate sample stream 11 in the conduit in an amount sufficient to prevent condensation of the $H_2O$ in the reformate sample stream in the conduit, i.e. using trace heating.

The method comprises dividing the reformate sample stream 11 into a vapor fraction-enriched stream 45 having a time-averaged mass flow rate $F_1$, and a liquid fraction-enriched stream 42 having a time-averaged mass flow rate $F_2$. The reformate sample stream may be divided by any known means, for example a pipe "T", with flow rates of each steam controlled by one or more valves.

Time-averaged mass flow rates are calculated in the conventional way from the generalized equation:

$$\bar{\xi} = \frac{1}{\tau} \int_{t_1}^{t_2} \xi(t) dt$$

$\bar{\xi}$ where his the time-averaged mass flow rate, $\xi$ is the instantaneous mass flow rate, t is time, where the specified quantity (i.e. first, second, third, etc.) flows from $t=t_1$ to $t=t_2$, where $t=t_1$ at the beginning of the flow of the specified quantity, $t=t_2$ at the end of the flow of the specified quantity, and where $\tau=t_2-t_1$.

The time-averaged mass flow rates $F_1$ and $F_2$ may be controlled such that $$\frac{F_1}{F_1 + F_2} \leq 0.2$$

where $F_1$ is nonzero. This means that only a reduced fraction of the original stream is used and further processed for later measurements in the chemical component analyzer 90. This allows for a larger flow rate of the sample passing from the source to the first heat exchanger 40 which has the advantages of decreasing the risk of condensation in the conduit from the source, increasing the sample response speed by decreasing the residence time of the sample gas from the source to the conditioning system and chemical component analyzer 90. This also has the advantage of concentrating the hydrocarbon components.

Since ammonia is soluble in liquid water, some of the ammonia present in the reformate sample stream 11 is removed with the liquid fraction-enriched stream 42. An advantage of taking the larger sample and condensing water with ammonia contained therein, is that a larger percentage of the ammonia is removed with the liquid fraction-enriched stream 42, thereby depleting ammonia in the vapor fraction-enriched stream 45.

Condensing water from the reformate sample stream 11 followed by dividing the stream into the liquid fraction-enriched stream 42 and the vapor fraction-enriched stream 45 has a combined effect that reduces the ammonia loading to the ammonia removal unit 70, discussed below.

The method comprises cooling the vapor fraction-enriched stream 45 to within a temperature ranging from 0° C. to 10° C. or ranging from 2° C. to 7° C. to condense $H_2O$ in the vapor fraction-enriched stream. The vapor fraction-enriched stream may be cooled in a second heat exchanger 60 wherein the second heat exchanger 60 comprises a vortex tube wherein compressed air is introduced into the vortex tube to provide the cooling of the vapor fraction-enriched stream.

The method comprises removing at least a portion of the condensed $H_2O$ 62 from the vapor fraction-enriched stream 45 thereby forming the vapor fraction-enriched stream 45 with a portion of water removed therefrom. The at least a portion of the condensed $H_2O$ 62 may be removed from the vapor fraction-enriched stream 45 using a liquid drain trap 65 and optionally a coalescing filter (not shown). Liquid drain traps are available commercially, for example, from Armstrong International.

The two-stage condensation in the first heat exchanger 40 and second heat exchanger 60 addresses the problem related to the high water content in reformate streams. Unexpectedly, the water removal does not appreciably affect the concentration of the hydrocarbons in the vapor fraction-enriched stream 45.

The method comprises passing the vapor fraction-enriched stream 45 having a portion of water removed therefrom to an ammonia removal unit 70 to remove $NH_3$ from the vapor fraction-enriched stream 45 thereby forming the vapor fraction-enriched stream 45 with ammonia removed therefrom. The ammonia may be removed by any known means. The ammonia may, for example, be removed by chemical reaction with a scrubber media in ammonia scrubber 70. Any scrubber media known to remove ammonia may be used. The ammonia scrubber media may comprise phosphoric acid. The ammonia scrubber 70 may be, for example, an AS™-Series Ammonia Scrubber commercially available from Perma Pure, LLC.

Ammonia should be removed because ammonia may deactivate the membrane dryer and shorten the active life of the membrane dryer. Ammonia may also cause adhesives inside the gas chromatograph to fail if samples having greater than 100 ppmv are introduced into the gas chromatograph.

While it may be desirable to remove all of the ammonia, low ppmv levels of ammonia may still be present in the vapor fraction-enriched stream after passing the stream through the ammonia removal unit 70. Since complete removal of ammonia may not be possible, and substantial removal of ammonia (<10 or <100 ppmv) is acceptable for downstream devices, as used herein, "to remove ammonia" does not mean complete removal of ammonia. Ammonia may be removed in an amount such that the vapor fraction-enriched stream has an ammonia content less than 5 ppmv.

The method may further comprise passing the vapor fraction-enriched stream 45 from the ammonia removal unit 70 to a dryer 80 to further remove $H_2O$ in the vapor fraction-enriched stream 45 thereby forming the vapor fraction-enriched stream 45 with further removal of water. The dryer 80 may be a membrane dryer. The dryer 80 may be a PRISM® Membrane Dryer commercially available from Air Products and Chemicals, Inc. or a membrane dryer commercially available from Perma Pure. When the dryer 80 is a membrane dryer, dry $N_2$ or dry air may be introduced into the membrane dryer as a purge gas to assist in the removal of $H_2O$ from the vapor fraction-enriched stream 45.

While it may be desirable to remove all of the water, low vol. % levels of water may still be present in the vapor fraction-enriched stream after passing the stream through the dryer 80. Since complete removal of water may not be possible, and substantial removal of water (<1 vol. %) is acceptable for downstream devices, as used herein, "to further remove water" does not mean complete removal of water. Water may be removed in an amount such that the vapor fraction-enriched stream has a water content less than about 0.3 vol. %.

The vapor fraction-enriched stream 45 may be passed to a filter 83, where a filtered first portion 85 is passed to the chemical component analyzer 90 and an unfiltered second portion 82 is rejected to a vent and flared or otherwise disposed of. The method may comprise rejecting the second portion 82 of the vapor fraction-enriched stream 45 where the second portion is not passed to the chemical component analyzer 90. The first portion 85 of the vapor fraction-enriched stream may be introduced intermittently into the chemical component analyzer 90. The first portion 85 of the vapor fraction-enriched stream 45 has a time-averaged mass flow rate, $V_1$, and the second portion of the vapor fraction-enriched stream has a time-averaged mass flow rate, $V_2$. (Time-averaged mass flow rates are defined above).

The time-averaged mass flow rates $V_1$ and $V_2$ may be controlled such that $$\frac{V_1}{V_1 + V_2} \leq 0.1$$

where $V_1$ is nonzero. This means that only a reduced fraction of the vapor-fraction enriched stream is used in the chemical component analyzer 90.

The method further comprises passing at least a first portion 85 of the vapor fraction-enriched stream 45 from the dryer 80 to a chemical component analyzer 90 to measure the hydrocarbon content in the at least a first portion 85 of the vapor fraction-enriched stream 45. The C2+ hydrocarbon content may be, for example, a concentration of C2+ hydrocarbons, or a ratio with one of the other components in the first portion 85.

The chemical component analyzer 90 may be a gas chromatograph (GC). The gas chromatographs have been found to be accurate for measuring hydrocarbon concentrations from ppm levels to percent levels (trace to major species).

The chemical component analyzer 90 may be a mass spectrometer. The chemical component analyzer 90 may be a non-methane hydrocarbon analyzer, which uses a flame ionization detector, for example, as available from Baseline—MOCON, Inc. The chemical component analyzer 90 may be a tunable diode laser analyzer, for example, as available from Yokogawa.

The liquid fraction-enriched stream 42 may be further cooled in heat exchanger 50, which may be an air-cooled heat exchanger. Water 57 may be collected in a liquid drain trap 55 and disposed of. An ammonia-containing vapor stream 59 may be vented or flared or otherwise disposed of. The benefit of further removing water from the liquid fraction-enriched stream 42 is that the ammonia-containing vapor stream 59 can be more reliably flared.

I claim:

1. A method for characterizing a hydrocarbon content of a reformate sample stream, the method comprising:
   (a) withdrawing the reformate sample stream from a steam-hydrocarbon reforming process, the reformate sample stream comprising $CH_4$, $H_2O$, $CO$, $NH_3$, and $H_2$;
   (b) cooling the reformate sample stream in a first heat exchanger to condense a portion of the $H_2O$ in the reformate sample stream thereby forming a liquid fraction and a vapor fraction;
   (c) dividing the reformate sample stream from step (b) into a vapor fraction-enriched stream having a time-averaged mass flow rate, $F_1$, and a liquid fraction-enriched stream having a time-averaged mass flow rate, $F_2$;
   (d) cooling the vapor fraction-enriched stream to within a temperature ranging from 0° C. to 10° C. to condense $H_2O$ in the vapor fraction-enriched stream;
   (e) removing at least a portion of the condensed $H_2O$ from the vapor fraction-enriched stream from step (d);
   (f) passing the vapor fraction-enriched stream from step (e) to an ammonia removal unit to remove $NH_3$ from the vapor fraction-enriched stream; and
   (g) passing at least a first portion of the vapor fraction-enriched stream from step (f) to a chemical component analyzer to measure the hydrocarbon content in the at least a first portion of the vapor fraction-enriched stream.

2. The method of claim 1 wherein the vapor fraction-enriched stream from step (f) is passed to a dryer to further remove $H_2O$ in the vapor fraction-enriched stream prior to passing the at least a first portion of the vapor fraction-enriched stream to the chemical component analyzer.

3. The method of claim 1 wherein $F_1$ and $F_2$ are controlled such that $$\frac{F_1}{F_1 + F_2} \leq 0.2.$$

4. The method of claim 1 wherein the vapor fraction-enriched stream is cooled in step (d) to within a temperature ranging from 2° C. to 7° C.

5. The method of claim 1 further comprising passing the reformate sample stream through a conduit from a reformate sample stream source to the first heat exchanger while heating the reformate sample stream in the conduit in an amount sufficient to prevent condensation of the $H_2O$ in the reformate sample stream in the conduit.

6. The method of claim 1 wherein the at least a portion of the condensed $H_2O$ from the vapor fraction-enriched stream is removed using a liquid drain trap.

7. The method of claim 1 wherein the at least a portion of the condensed $H_2O$ from the vapor fraction-enriched stream is removed using a liquid drain trap and a coalescing filter.

8. The method of claim 1 wherein the ammonia removal unit comprises phosphoric acid.

9. The method of claim 1 further comprising: rejecting a second portion of the vapor fraction-enriched stream from step (f) where the second portion is not passed to the chemical component analyzer, wherein the at least a first portion of the vapor fraction-enriched stream has a time-averaged mass flow rate $V_1$, the second portion of the vapor fraction-enriched stream has a time-averaged mass flow rate, $V_2$, where $$\frac{V_1}{V_1 + V_2} \leq 0.1.$$

10. The method of claim 1 wherein the vapor fraction-enriched stream is cooled in step (d) in a second heat exchanger wherein the second heat exchanger comprises a vortex tube wherein compressed air is introduced into the vortex tube to provide the cooling of the vapor fraction-enriched stream.

11. The method of claim 2 wherein the dryer is a membrane dryer.

12. The method of claim 11 wherein dry $N_2$ or dry air is introduced into the membrane dryer as a purge gas to assist in the removal of $H_2O$ from the vapor fraction-enriched stream.

13. The method of claim 1 wherein the reformate sample stream has an $H_2O$ mole fraction greater than 0.35.

14. The method of claim 1 wherein the chemical component analyzer is a gas chromatograph.

* * * * *